United States Patent
Nösberger

(10) Patent No.: US 6,288,243 B1
(45) Date of Patent: Sep. 11, 2001

(54) PROCESS FOR PURIFYING L-ASCORBYL 2-MONOPHOSPHATE

(75) Inventor: Paul Nösberger, Birsfelden (CH)

(73) Assignee: Roche Vitamins Inc., Parsippany, NJ (US)

(*) Notice: Subject to any disclaimer, the term of this patent is extended or adjusted under 35 U.S.C. 154(b) by 0 days.

(21) Appl. No.: 09/583,254

(22) Filed: May 31, 2000

(30) Foreign Application Priority Data

Jun. 7, 1999 (EP) .................................................. 99110851

(51) Int. Cl.[7] .................................................. C07F 9/06
(52) U.S. Cl. .................................................. 549/222
(58) Field of Search ............................................... 549/222

(56) References Cited

U.S. PATENT DOCUMENTS

| | | |
|---|---|---|
| 4,179,445 | 12/1979 | Sieb et al. . |
| 4,647,672 | 3/1987 | Seib et al. . |
| 4,724,262 | 2/1988 | Shimbo et al. . |
| 4,999,437 | 3/1991 | Dobler et al. . |
| 5,110,950 | 5/1992 | Seib et al. . |
| 5,420,302 | 5/1995 | Kaiser et al. . |
| 6,063,937 | 5/2000 | Dlubala et al. . |

OTHER PUBLICATIONS

Chemical Abstracts, vol. 110, No. 7, 110:58008q (Feb. 13, 1989).

English language translation of Japanese Kokai Patent Application No. 59–106494 (1984).

English language translation of Japanese Kokai Patent Application No. 59–51293 (1984).

Lee, et al., "Chemical Synthesis of Several Phosphoric Esters of L–Ascorbic Acid," *Carbohydrate Research*, vol. 67, pp. 127–138 (1978).

*Primary Examiner*—Floyd D. Higel
*Assistant Examiner*—Ebenezer Sackey
(74) *Attorney, Agent, or Firm*—Stephen M. Haracz; Kevin C. Hooper; Bryan Cave LLP

(57) ABSTRACT

A process for separating L-ascorbyl 2-monophosphate from a mixture of the products of the desalting of the product mixture obtained from the phosphorylation under basic conditions of an L-ascorbic acid salt is described. This process is characterized by passing an aqueous solution of the desalted mixture containing among other components the desired L-ascorbyl 2-monophosphate through a column of a basic anion exchange resin, with resulting adsorption of the components onto the resin, desorbing among other adsorbed components the L-ascorbyl 2-monophosphate from the resin using as the eluent an aqueous alkali hydroxide solution, and collecting from the eluate the fraction which contains as its principal dissolved component the desired L-ascorbyl 2-monophosphate in the form of the appropriate mono-alkali metal salt. The so obtained L-ascorbyl 2-monophosphate is especially stable against thermal and oxidative degradation compared with L-ascorbic acid (vitamin C) itself, and is thus suitable as a more stable form of ascorbic acid for use as an additive for foodstuffs, animal feeds and cosmetic products.

19 Claims, No Drawings

PROCESS FOR PURIFYING L-ASCORBYL 2-MONOPHOSPHATE

FIELD OF THE INVENTION

The present invention concerns a process for purifying L-ascorbyl 2-monophosphate wherein this substance, in the form of its mono-alkali metal salt, is recovered from a mixture of its alkali metal and alkaline earth metal salts, salts of other phosphorylated forms of L-ascorbic acid, and various alkali metal and/or alkaline earth metal phosphates using a basic anion exchange resin.

BACKGROUND OF THE INVENTION

As is known, ascorbic acid (vitamin C) and its salts are used as additives for foodstuffs, animal feeds, and cosmetic products. Ascorbic acid itself is sensitive to heat and oxidation, as a result of which it has the undesirable tendency to readily decompose. Accordingly, it is unsuitable in this form in many applications, e.g. in cosmetic products, and interest has developed in producing derivatives of ascorbic acid which have increased stability and which can replace ascorbic acid in the same applications.

It is also well known that ascorbic acid phosphates (ascorbyl phosphates) represent protected forms of ascorbic acid which are less susceptible to thermal and oxidative degradation. The use of such ascorbic acid derivatives, which are substantially more stable than ascorbic acid itself, almost completely eliminates the problem of decomposition or degradation. Ascorbic acid, which is the biologically active moiety, is liberated from such derivatives in the host organism by the action of the enzyme phosphatase.

Two fundamentally different processes have hitherto been of significance for the phosphorylation of ascorbic acid, namely phosphorylation using phosphorus oxychloride (as described, for example, in U.S. Pat. Nos. 4,999,437 to Dobler, et al. (Dobler '437), 5,420,302 to Kaiser, et al. (Kaiser '302), and 4,179,445 to Seib, et al. (Seib '445)) and phosphorylation using polyphosphates, e.g. sodium trimetaphosphate (see, for example, U.S. Pat. Nos. 4,647,672 to Seib, et al. (Seib '672) and 5,110,950 to Seib, et al. (Seib '950), and European Patent Publication 866,069), an L-ascorbic acid salt being phosphorylated under basic conditions in both cases.

The first phosphorylation process set forth above yields ascorbyl 2-monophosphate as the main product, and as by-products mainly ascorbyl 3-phosphate, 2-pyrophosphate, and bis(ascorbyl)-2,2'-diphosphate (see C. H. Lee et al., Carbohydrate Res. 67, 127–138 (1978)). In the past, the reaction products have required complicated purification and could not be converted in a simple manner, e.g. by spray drying of the entire reaction mixture, into a commercially useable product.

The second process, i.e. phosphorylation using polyphosphates, yields in the case of Seib '672 and Seib '950, ascorbyl 2-polyphosphates as the primary products, for example ascorbyl 2-triphosphate when sodium trimetaphosphate is used, but also a certain proportion of ascorbyl 2-monophosphate. The ascorbyl 2-polyphosphates can be degraded to the monophosphate by an excess of base. The ratio of ascorbyl 2-monophosphate to ascorbyl 2-diphosphate and higher polyphosphates is influenced by the amount of base which is used and the other reaction conditions. A disadvantage of the processes described above is that a very large amount of phosphorylating agent, e.g. at least 1 mol of sodium trimetaphosphate per mol of ascorbic acid, is required. Moreover, when it is desired that the product contain relatively small amounts of ascorbyl polyphosphates and more ascorbyl 2-monophosphate, a large amount of base, e.g. calcium hydroxide, must be used. Accordingly, the product contains a large amount of inorganic phosphates; the content of ascorbic acid equivalents in a dried product amounts to a maximum of about 25 weight percent.

Another process for the phosphorylation of L-ascorbic acid using polyphosphates is disclosed in European Patent Publication No. 866,069. In this process, the L-ascorbyl 2-polyphosphate, which itself may be produced separately or in situ by phosphorylating an alkali metal or alkaline earth metal salt of L-ascorbic acid with a phosphorylating agent such as sodium trimetaphosphate, is reacted with the L-ascorbic acid salt in concentrated aqueous solution under alkaline conditions using such amounts of the L-ascorbic acid salt and alkaline earth metal hydroxide (used as the base) that the pH value of the reaction medium is maintained in the range of about 8 to 11. In this reaction, a stepwise transfer of phosphate groups from the polyphosphate to the L-ascorbic acid salt occurs until the L-ascorbic acid from both sources is mainly in the form of its 2-monophosphate salt. Although this process affords the L-ascorbyl phosphate salt with very high monophosphate content and thus a much higher content of ascorbic acid equivalents in the dried product than achieved with the previously developed processes, the product still inevitably contains some unreacted starting materials and by-products, in particular non-phosphorylated ascorbate, ascorbyl di- and higher phosphates (ascorbyl polyphosphates), and orthophosphate and pyrophosphate (inorganic phosphates).

The relative proportion of the desired ascorbyl monophosphate to the ascorbyl polyphosphates, non-phosphorylated ascorbate, inorganic phosphates, etc., resulting from the processes described above depends on the stoichiometric ratios in which the starting materials are employed and on the other reaction conditions, and is never completely satisfactory. The recovery of L-ascorbyl 2-monophosphate or its inorganic salts from mixtures thereof with the unreacted starting materials and the by-products, i.e. the purification of L-ascorbyl 2-monophosphate, is difficult, in particular because the components of such mixtures largely feature similar physical properties. For example, they are all practically insoluble in organic solvents. In water, however, the free acids and the sodium salts, for example, are readily soluble, whereas the calcium salts are sparingly soluble. Thus purification by crystallization is rendered impracticable.

L-ascorbyl 2-phosphate purification procedures also have been described previously. For example, Japanese Patent Publication (Kokai) 51293/1984 describes the purification of L-ascorbyl 2-phosphate using an activated charcoal column and an aqueous solution of phosphoric acid and ammonium hydroxide as the eluent, followed by passage of the eluate through a column of a strong cation exchange resin to remove ammonium ions followed by treatment with magnesium oxide to remove excess phosphoric acid as its magnesium salt. The resulting L-ascorbyl 2-phosphate in the pure magnesium salt form is purified again with activated charcoal and crystallized from methanol.

Another Japanese Patent Publication (Kokai) 106,494/1984 describes an ascorbyl phosphate purification process involving, as an alternative to activated charcoal, diatomaceous earth or acid clay, and a precipitation in an organic solvent. However, it is known that active charcoal and the aforementioned alternative media are suitable for removing colored substances, but not for removing the by-products of ascorbic acid phosphorylation. Shimbo, et al., U.S. Pat. No. 4,724,262 (Shimbo '262), in which both these Kokai are briefly reviewed, discloses further disadvantages of the processes described therein. The process of purifying L-ascorbyl 2-phosphate described in Shimbo '262 involves the use of a basic anion exchange resin as an adsorbent for, inter alia, the aforementioned desired component, which is subsequently eluted with an aqueous solution of a mineral acid or an inorganic salt. This process is disadvantageous, however, because the acid or salt solution for the elution saturates the anion exchange resin, which must subsequently be regenerated with a base, such as sodium hydroxide solution. This leads to unnecessary and ecologically undesirable salt solutions.

SUMMARY OF THE INVENTION

Before a mixture of alkali metal and alkaline earth metal salts of L-ascorbyl phosphates (mono- and polyphosphates) produced by the phosphorylation of ascorbic acid under basic conditions can be separated into its components on an anion exchange resin for ultimate isolation of a desired component of such a mixture, particularly the L-ascorbyl 2-monophosphate, the mixture must be converted to one containing essentially the pertinent free acids, the metal ions having been replaced with hydrogen ions. Such a "desalting" is in principle already known, e.g. from some of the patent literature reviewed hereinabove, whereby a strongly acidic cation exchange resin is employed. The result of such a desalting is normally an aqueous solution of L-ascorbic acid, L-ascorbyl mono- and polyphosphates, bis-(L-ascorbyl) phosphate and phosphoric acids (mainly ortho- and pyrophosphoric acid; referred to herein, to avoid confusion with the L-ascorbyl mono- and polyphosphates, as the inorganic phosphoric acids). Accordingly, one object of the present invention is to isolate L-ascorbyl 2-monophosphate from the remaining aforementioned and other components of such mixtures.

One embodiment of the present invention is a process for separating L-ascorbyl 2-monophosphate from a desalted product mixture obtained from phosphorylation of an L-ascorbic acid salt under basic conditions comprising:

(a) contacting an aqueous solution of the desalted mixture containing L-ascorbyl 2-monophosphate with a basic anion exchange resin in a separation vessel, wherein the L-ascorbyl 2-monophosphate is adsorbed to the resin;

(b) eluting the L-ascorbyl 2-monophosphate from the resin with an aqueous alkali hydroxide solution; and (c) isolating the L-ascorbyl 2-monophosphate in an appropriate monoalkali metal salt form from a fraction of the eluate which contains as its principal dissolved component said L-ascorbyl 2-monophosphate in an appropriate mono-alkali metal salt form.

Another embodiment of the invention is a process for separating L-ascorbyl 2-monophosphate from a desalted product mixture obtained from phosphorylation of an L-ascorbic acid salt under basic conditions. This process includes contacting an aqueous solution of the desalted mixture containing L-ascorbyl 2-monophosphate with a basic anion exchange resin in a separation vessel, wherein the L-ascorbyl 2-monophosphate is adsorbed to the resin. Next, the L-ascorbyl 2-monophosphate is eluted from the resin with an aqueous alkali hydroxide solution. Then, the L-ascorbyl 2-monophosphate is isolated in an appropriate mono-alkali metal salt form from a fraction of the eluate which contains as its principal dissolved component the L-ascorbyl 2-monophosphate.

DETAILED DESCRIPTION OF THE INVENTION

It has now been found that the desired L-ascorbyl 2-monophosphate in such a mixture can be separated from the other components of the mixture by passing an aqueous solution of the mixture, which has previously been desalted by treatment with a strongly acidic cation exchange resin, through a basic anion exchange resin which adsorbs among other components the L-ascorbyl 2-monophosphate, then progressively freeing, i.e. desorbing (sometimes also described as regenerating), the adsorbed components from the basic anion exchange resin by subsequent passage therethrough of an aqueous alkali hydroxide solution and collecting from the eluate the fraction which contains as its principal dissolved component the L-ascorbyl 2-monophosphate in the form of an appropriate mono-alkali metal salt. In particular, the invention resides in the use of the aqueous alkali hydroxide solution as the eluting agent (eluent) to desorb the L-ascorbyl 2-monophosphate from the basic anion exchange resin onto which this component, among others, has been adsorbed.

Accordingly, the present invention provides a process for separating L-ascorbyl 2-monophosphate from a mixture of the products of the desalting of the product mixture obtained from the phosphorylation under basic conditions of an L-ascorbic acid salt, which process is characterized by passing an aqueous solution of the desalted mixture containing among other components, the desired L-ascorbyl 2-monophosphate, through a column of a basic anion exchange resin with resulting adsorption of the components onto the resin, desorbing along with the other adsorbed components the L-ascorbyl 2-monophosphate from the resin using as the eluent an aqueous alkali hydroxide solution, and collecting from the eluate the fraction which contains as its principal dissolved component the desired L-ascorbyl 2-monophosphate in the form of the appropriate mono-alkali metal salt.

The starting material for the process of the present invention may be any mixture of products of a process involving the phosphorylation, under basic conditions, of an L-ascorbic acid salt, particularly an alkali metal, alkaline earth metal or mixed alkali metal/alkaline earth metal salt, to produce an appropriate L-ascorbyl 2-monophosphate salt, or any partially purified product, e.g. one isolated through crystallization, whereby such un- or partially purified product has subsequently been desalted as explained hereinabove. Conventional phosphorylation processes, for example those set forth above, may be used to provide the starting material for the process of the present invention. The desalting may be performed by any conventional process, such as for example by treatment of a phosphorylation product mixture or partially purified product with a cation exchange resin, as described for example in Shimbo '262.

In the present invention, the desalting serves to remove the metal ions, particularly sodium and calcium ions and such heavy metal ions as manganese, iron, zinc and strontium ions which may be present in the phosphorylation product. Passage of a phosphorylation product mixture or a partially purified product in aqueous medium through a cation exchange resin converts the various metal salt forms of ascorbic acid, ascorbyl mono- and polyphosphates and inorganic phosphoric acids into the corresponding free acids.

When the phosphorylation is effected with sodium trimetaphosphate under the basic conditions provided by an alkaline earth metal hydroxide, particularly calcium hydroxide, such as for example using the process of European Patent Publication No. 866,069, the product mixture contains alkaline earth metal salts which are only partially soluble in water. Clarification of such a solution is achieved after removal of the alkaline earth metal ions. Accordingly, desalting is conveniently carried out in such cases in two steps. In the first step, the alkaline earth metal and some of the alkali metal ions are removed in a stirred or fluidized bed of cation exchange resin. In the second step, the resulting clear solution is passed through a fixed resin bed to remove the remaining alkali metal ions and thus complete the desalting. For the first desalting step, a mechanically stable sulphonic acid exchange resin is used, such as AMBERLITE® 200 C, DUOLITE® C 265 and Imac C 16 P (Rohm & Haas), DOWEX® MSC-1 (Dow Chemical), PUROLITE® C 160 (Purolite Int.), LEWATIT® C 120 (Bayer) and RELITE® C 360 (Mitsubishi). Both liquid and solid, e.g. spray dried, phosphorylation products can be used. The exchange capacity of the resin should generally be from about 100% to about 300% of the calculated amount of the metals to be removed. The second desalting step is preferably effected in a fixed resin bed with countercurrent regeneration. The exchange capacity of the employed cation exchange resin is, in this case too, suitably from about 100% to about 300% of the calculated amount of the metals to be removed. The same kinds of cation exchange resins set forth above for the first desalting step can be used in the second desalting step.

The aqueous solution containing the desalted mixture which elutes from the cation exchange resin can then be submitted to the process of the present invention. The solids (acids) content of such an aqueous solution is suitably in the range from about 5% to about 20% by weight, and the pH of the aqueous solution is generally about 0.7. In view of the relative instability of the aqueous solution at this pH, it is processed in the present process through a basic anion exchange resin, followed by adsorption, and desorption with aqueous alkali hydroxide solution as the eluent, without undue delay, thereby avoiding undesired deterioration (degradation) through prolonged storage.

The basic anion exchange resin used in the process of the present invention includes any basic anion exchange resin which features functional groups such as for example primary, secondary or tertiary amines or quaternary ammonium groups. Basic ion exchange resins which feature amine groups as the functional groups are generally considered to be weakly basic, and those which feature quaternary ammonium groups are generally considered to be strongly basic. The weakly basic anion exchange resins are preferred to the strongly basic ones in the present invention. Especially preferred are weakly basic anion exchange resins which tend to swell as little as possible when contacted with the aqueous solution of the desalted mixture containing the L-ascorbyl 2-monophosphate. Macroreticular, weakly basic anion exchange resins based on styrene-divinylbenzene display such preferred characteristics and are therefore preferred as the basic anion exchange resins in the process of the present invention.

Examples of such weakly basic anion exchange resins, all of which are commercially available, are AMBERLITE® IRA 96 SB and IRA 96 RF, and DUOLITE® A 561 and A7 (Rohm & Haas), LEWATIT® MP 62 (Bayer) and DOWEX® MWA-1 (Dow Chemicals). Of these, AMBERLITE® IRA 96 SB, LEWATIT® MP 62 and DOWEX® MWA-1 are especially preferred.

It has been established that on such basic anion exchange resins the order of the strength of adsorption of the various desalted components of the mixture which in aqueous medium are passed therethrough is as follows (more strongly→less strongly adsorbed):

L-ascorbyl polyphosphates>pyrophosphoric acid>L-ascorbyl 2-monophosphate1 bis-(L-ascorbyl) phosphate>orthophosphoric acid>L-ascorbic acid Thus, the ascorbic and orthophosphoric acids are adsorbed onto the basic anion exchange resin more weakly than the desired L-ascorbyl 2-monophosphate, and the pyrophosphoric acid and L-ascorbyl polyphosphates more strongly, so that on desorption with an aqueous alkali hydroxide solution, the order in which these components are successively eluted and collected as fractions is from less (first) to more strongly (last) adsorbed components. Thus, L-ascorbyl 2-monophosphate is desorbed and eluted at an intermediate stage during the desorption process.

Also adsorbed to some extent are the components present in small amounts which impart color to the mixture in aqueous medium (hereinafter referred to as "colored components"). Those colored components which are adsorbed less strongly are desorbed with the L-ascorbic acid, and the more strongly adsorbed ones are desorbed with the L-ascorbyl polyphosphates.

The amount of basic anion exchange resin employed depends, among other known factors, on the exchange capacity of the resin and the amount of mixture components in the aqueous medium intended to be adsorbed onto the resin. As is generally known in the art, the amount of mixture components in acid form should not exceed the total exchange capacity of the particular resin being used. Conveniently, 1 liter of the basic anion exchange resin is employed for about 0.5 to about 1.5 moles of the total acid components. A much higher proportion of resin volume:moles of total acid components can of course be used, but becomes increasingly uneconomical as it increases.

The amount of water in which the acid components of the mixture are dissolved is conveniently in the range of about 1 to about 5 volumes per volume of resin.

Once the aqueous solution of the desalted product mixture has been passed into the basic anion exchange resin, with resulting immediate adsorption of acid components, it has been found to be advantageous to precede the passage of the aqueous alkali hydroxide solution by passing water through the resin. The subsequent passage of the alkali hydroxide solution activates the separation of (desorbs) the adsorbed acid components. The aqueous alkali hydroxide solution is suitably aqueous sodium hydroxide or aqueous potassium hydroxide solution, of which the former is preferred. The alkali hydroxide solution conveniently has a concentration in the range of about 3% to about 6% by weight. Preferably, this concentration is in the range from about 4% to about 5% by weight. The amount of aqueous alkali hydroxide solution passed through the resin depends, inter alia, on the concentration of this solution, the nature of the acid components adsorbed on the resin and the adsorption capacity of the resin. In general, the amount of alkali hydroxide must exceed the resin capacity by e.g. about 50%. Conveniently, from about 1.5 to about 2.0 moles of alkali hydroxide are passed through the resin per mole of total capacity of the resin with adsorbed components of the desalted mixture. The total capacity of a commercially obtainable basic anion exchange resin is generally specified by the manufacturer in each case and is usually expressed as a minimum value in moles/liter of resin. Furthermore, the concentration of the aqueous alkali hydroxide solution determines the concentration of the components in the fractions of the eluate. For example, using a 4% aqueous sodium hydroxide solution results in the fraction of the eluate containing principally L-ascorbyl 2-monophosphate in the form of its monosodium salt with a concentration of about 20%.

The speed with which the liquid flows through the resin column, i.e. the rate of flow or the fluid velocity, is conveniently in the range from about 0.5 to about 2 bed volumes/hour.

In the present invention, the terms "column," "resin column," and "separation vessel" are used interchangeably. As used herein, "separation vessel" means any container suitable for the types of separation processes described herein, such as for example columns of the type used in gravity flow and higher pressure liquid chromatography (HPLC).

The change in density and optical properties of the eluate during the progress of the elution results from the changing content of the eluate, i.e. the extent to which any particular component is present in the eluate at each stage of the total elution. This can form the basis upon which fractions are collected. These fractions each contain one or several regenerated components in predominance. At some stage in the elution, the eluate contains predominantly the desired L-ascorbyl 2-monophosphate mono-alkali metal salt as the dissolved component. By monitoring the density or optical properties, e.g. optical rotation, one is able to determine the cut-off points between the fractions and collect or redirect the ones required either for recycling to the phosphorylation process or ion exchange separation process or for further treatment to ultimately isolate the component of interest. The fraction which on the basis of density, an optical property or some other characterizing parameter contains predominantly, if not solely, the desired L-ascorbyl 2-monophosphate mono-alkali metal salt as the dissolved component is collected. Fractions which contain predominately L-ascorbic acid or L-ascorbyl di- and/or higher polyphosphates are conveniently recycled by means known in the process technology arts to the phosphorylation process for producing further ascorbyl monophosphate. Those fractions which contain mixtures of the L-ascorbyl 2-monophosphate salt and one or more further components as dissolved components whereby the proportion of the ascorbyl monophosphate salt is insufficiently high are conveniently recycled to the ion exchange separation process with a view to ultimately collecting an eluate fraction containing the ascorbyl monophosphate salt as the predominant or sole dissolved component. Alternatively, they can be recycled to the phosphorylation process.

Once the aqueous alkali hydroxide solution has been passed through the weakly basic anion exchange resin, any remaining solution is conveniently displaced by passage of water through the resin. This serves to complete the preparation of the resin for the round of desalting. The volume of water used at this stage is conveniently from about 0.5 to about two times the volume of the resin. A larger volume of water may be used with no economical advantage because the eluate ultimately consists of water with no or hardly any dissolved component.

The ion exchange separation process of the present invention is conveniently effected at room temperature, or if this is higher than about 30° C., at temperatures not exceeding about 30° C., in order to avoid the deterioration by degradation of the components undergoing separation.

After the eluate fraction containing the desired L-ascorbyl 2-monophosphate as its mono-alkali metal salt and as the predominant or sole dissolved component has been collected, it is conveniently processed as follows:

The collected fraction of the eluate containing the monoalkali metal salt of L-ascorbyl 2-monophosphate, of about pH 3, is conveniently neutralized with aqueous alkali hydroxide solution to a pH value in the range from about 9 to about 9.5 or from about 6 to about 7, and optionally concentrated to an extent appropriate for the next or final step. Thereafter the optionally concentrated, neutralized solution is conveniently spray dried or treated with a lower alkanol, e.g. methanol or ethanol, to effect crystallization of the L-ascorbyl 2-monophosphate in the form of its alkali metal, particularly sodium, salt.

In the neutralization step, the alkali hydroxide of the aqueous solution used is conveniently the same as the one used in the eluent for the desorption from the basic anion exchange resin. In this way, the production of a mixed alkali metal salt is avoided. Accordingly, the alkali hydroxide is preferably sodium hydroxide. The concentration of the aqueous alkali hydroxide solution is suitably in the range from about 20% to about 50% by weight. The use of such relatively concentrated aqueous alkali hydroxide solution is preferred to avoid concentrating the neutralized solution in the optional following step more than necessary. Neutralization to a pH of about 9 to 9.5 produces the tri-alkali metal salt (full neutralization) and to a pH of about 6 to 7 the di-alkali metal salt (partial neutralization). Because the latter salt is relatively unstable compared with the former salt, neutralization to a pH of about 9 to 9.5 is preferred. In any event, such neutralization and the specific techniques for performing it are known.

As regards the optionally performed concentration of the neutralized solution of L-ascorbyl 2-monophosphate, several known techniques are available, e.g. the use of a falling film evaporator. Thereby the volume is conveniently reduced to about 40% to 50% of the starting volume. In this case too, the person skilled in the art is well able to employ an appropriate technique and to monitor the desired extent of concentration.

The crystallization may be performed in various ways, including for example (1) the addition of the alkanol to the optionally concentrated, neutralized solution of the L-ascorbyl 2-monophosphate alkali metal salt, (2) addition of the optionally concentrated, neutralized solution of L-ascorbyl 2-monophosphate alkali metal salt to the alkanol, or (3) the simultaneous introduction of both liquid components into the crystallization vessel. Whereas the first and second methods are more appropriate to batch processes, the third method is more suitable for a continuous process. In an example of the second method, the crystallization is conveniently performed by adding the optionally concentrated aqueous solution of the L-ascorbyl 2-monophosphate salt to the lower alkanol, preferably methanol, at elevated temperature, slowly at the beginning and increasingly faster towards the end of the addition. Temperatures up to within 10 Centigrade degrees of the boiling point of the aqueous/organic mixture are generally suitable. Furthermore, it is convenient to agitate the solution during the addition, particularly by stirring, and to continue the stirring at the elevated temperature for up to about an hour after the completion of the addition. Thereafter, the resulting slurry of crystals is conveniently cooled down to ambient temperature and stirred for a further period, preferably about an hour, before the crystals are separated off. Irrespective of the crystallization methodology employed, the resulting crystals may be separated off by a standard technique such as filtration or centrifugation. Drying of the crystals may be performed if desired, also by standard techniques.

As an alternative to crystallization, the solid L-ascorbyl 2-monophosphate salt may be obtained by conventional spray drying of the optionally concentrated, neutralized solution.

The advantages of the inventive process are manifold, and include the following:

(1) colored components are removed;
(2) the aqueous alkali hydroxide solution used as the eluent not only serves to desorb the components adsorbed on the basic anion exchange resin, but also regenerates the resin for reuse;
(3) the L-ascorbyl 2-monophosphate mono-alkali metal salt separated in the process is obtained in aqueous solution at an economically high concentration; and
(4) the eluate fractions which do not contain predominantly L-ascorbyl 2-monophosphate mono-alkali metal salt can be recycled to the phosphorylation process for producing further ascorbyl monophosphate or to the ion exchange separation process for further separation of any ascorbyl monophosphate still present.

The following examples are provided to further illustrate the process of the present invention. These examples are illustrative only and are not intended to limit the scope of the invention in any way.

EXAMPLES

Example 1

Desalting of a Crude Mixture of Mixed Sodium/calcium Salts of L-ascorbyl 2-monophosphate and Other Components In accordance with the stirred resin methodology, 130 g of a crude mixture of reaction products from a process for producing a mixed sodium/calcium salt of L-ascorbyl 2-monophosphate containing mixed sodium/calcium salts of L-ascorbic acid (approx. 4%), L-ascorbyl monophosphate (approx. 62%), L-ascorbyl di- and other phosphates (approx. 6% and 9%, respectively), orthophosphoric acid (approx. 4%) and pyrophosphoric acid (approx. 8%) (obtained from the process set forth in European Patent Publication No. 866,069), and about 8% of water, were dissolved in a stirred suspension of 850 ml of a strongly acidic cation exchange resin (AMBERLITE® 200C, Rohm and Haas Deutschland GmbH, Frankfurt/Main) in 700 ml of water for about 30 minutes. The crude mixture included an L-ascorbic acid content of about 40%, of which about 10% was nonphosphorylated, about 80% was in the form of the monophosphate, about 3% was in the form of bis-(L-ascorbyl) phosphate and about 7% was in the form of L-ascorbyl polyphosphates. The resulting solution having a pH of about 3 was separated from the resin, and the latter was washed successively with two 500 ml portions of water. The solution and the two washings were then run successively through a column packed with 500 ml of a strongly acidic cation exchange resin. About 1800 g of a solution containing principally desalted L-ascorbyl 2-monophosphate with a pH of about 0.7 were collected. This solution, having an L-ascorbic acid content of about 3%, was employed as the aqueous solution of the desalted mixture for passage through the basic anion exchange resin as the first step in the process according to the present invention.

The foregoing procedure was repeated except that 700 ml, instead of 850 ml, of the strongly acidic cation exchange resin were present in the stirred suspension of resin in water, and after the dissolution period of about 80 minutes and separation of the solution the resin was washed successively with two 600 ml, instead of 500 ml, portions of water. Otherwise the procedure was analogous.

Example 2

Separation of L-ascorbyl 2-monophosphate From the Desalted Product Mixture

The solution from the desalting procedure described in Example 1, in either variation, was not collected but instead passed into a column filled with water and 300 ml of a weakly basic anion exchange resin (AMBERLITE® IRA 96 SB, Rohm and Haas Deutschland GmbH, Frankfurt/Main). Following this, the column was fed successively with 0.75 l of 3% aqueous sodium hydroxide solution for the desorption of the adsorbed components of the mixture and the regeneration of the anion exchange resin and with 1 l of water for displacement of the sodium hydroxide solution. During the resulting elution the density of the outflowing solution was measured.

Once the density of the eluate had reached a value exceeding 1.03 g/ml the collection of the product solution, i.e. the fraction of the eluate containing the desired L-ascorbyl 2-monophosphate, was commenced. 124 ml of this fraction were collected, then neutralized with 50% aqueous sodium hydroxide solution to pH 9.5 and finally evaporated to dryness. Analysis of the solid product gave an L-ascorbic acid content of 46.8%, of which 0.5% was non-phosphorylated, 97.3% was in the form of the monophosphate, 1.5% was in the form of bis-(L-ascorbyl) phosphate and 0.5% was in the form of L-ascorbyl diphosphate. No other polyphosphates were detected.

The foregoing procedure was repeated with the difference that DOWEX® MWA-1 (Dow (Europe) SA, CH-8810 Horgen, Switzerland) was used instead of AMBERLTE® IRA 96 SB as the weakly basic anion exchange resin. Analysis of the solid product obtained after elution, neutralization and evaporation to dryness gave an L-ascorbic acid content of 46.2%, of which 1.2% was non-phosphorylated, 97.5% was in the form of the monophosphate, 0.9% was in the form of bis-(L-ascorbyl) phosphate and 0.1% was in the form of L-ascorbyl disphosphate. Other polyphosphates were not detected.

Example 3

Desalting of a Crude Mixture of Mixed Sodium/calcium Salts of L-ascorbyl 2-monophosphate and Other Components The desalting apparatus consisted of a buffer vessel equipped with a stirrer, a circulation pump and an ion exchange column of total volume 8 l and which had been filled with water and 5.8 l of a strongly acidic cation exchange resin (AMBERLITIE® 200 C). In accordance with the fluidized resin methodology, 2 l of water were introduced into the buffer vessel and circulated by means of the circulation pump to the lower part of the ion exchange column and back to the buffer vessel. The speed of the water circulation was adjusted such that the cation exchange resin expanded by about 20% in volume.

1.26 kg of a solid crude mixture of reaction products was introduced into the buffer vessel over 30 minutes. This crude mixture was obtained from a process for producing a mixed sodium/calcium salt of L-ascorbyl 2-monophosphate (of the same composition as given for the crude mixture used as the starting material in Example 1 above).

After a further 30 minutes the solid crude mixture was fully dissolved, and the resulting solution had a pH of about 2.5.

This solution was then pumped into an ion exchange column filled with water and 3.8 l of a strongly acidic cation exchange resin (AMBERLIIE® 200 C) at a feed rate of 8 l/h. Then 8 l of water were introduced into the column for displacement of the solution. Through the contact with the resin, the sodium and calcium ions were completely separated from the dissolved components in the solution. The resulting desalted solution, of pH 0.7, was then be used for the separation of the L-ascorbyl 2-monophosphate using a basic anion exchange resin.

Example 4

Separation of L-ascorbyl 2-monophosphate From the Desalted Product Mixture

The solution from the desalting procedure of Example 3 was not collected but instead passed into a column filled with water and 3.6 l of a weakly basic anion exchange resin (AMBERLITE® IRA 96 SB). Following this, there were introduced successively into the column 2 l of water at a feed rate of 8 l/h for the displacement of the previously introduced solution, 7.5 l of a 4% aqueous sodium hydroxide solution at a feed rate of 4 l/h for the desorption of the adsorbed components, and 4 l of water at a feed rate of 8 l/h for the displacement of the sodium hydroxide solution, after which the anion exchange resin had been regenerated for the next use.

The following eluate fractions were collected from the column:

$1^{st}$ fraction, of density less then 1.01 g/ml, being 12 kg of water;

$2^{nd}$ fraction, of density 1.01–1.08 g/ml, being 2.5 kg of a solution A;

$3^{rd}$ fraction, of density greater than 1.08, being 3 kg of a solution B; and $4^{th}$ fraction, of density 1.08–1.045 g/ml, being about 3 kg of a solution C.

The solution A contained L-ascorbic acid, phosphoric acid and some L-ascorbyl 2-monophosphate in the form of its monosodium salt, and was recycled to the phosphorylation process for producing further ascorbyl monophosphate. The solution C contained, in addition to some ascorbyl monophosphate as its monosodium salt, pyrophosphoric acid and L-ascorbyl polyphosphates; it also was recycled to the phosphorylation process.

The solution B contained principally L-ascorbyl 2-monophosphate monosodium salt as the dissolved component. After neutralization with 28% aqueous sodium hydroxide solution to pH 9.5 the solution was analyzed by HPLC. According to the analysis the content of L-ascorbic acid was 18%, of which 1% was non-phosphorylated, 97% was in the form of the monophosphate, 1.5% was in the form of bis-(L-ascorbyl) phosphate and 0.5% was in the form of L-ascorbyl diphosphate. Other polyphosphates were not detected.

Example 5

Separation of L-ascorbyl 2-monophosphate From the Desalted Product Mixture

In this example, two ion exchange columns A1 and A2, each packed with 3.6 l of a weakly basic anion exchange resin (AMBERLITE® IRA 96 SB), were used in an alternating operational system.

The column A1 was in a state of preparedness for the adsorption of the mixture components and contained water in addition to the regenerated resin (in the OH form), whereas the column A2 contained the solution (D) from a previous run, so that its resin featured adsorbed ascorbyl and inorganic phosphates.

1 kg of the solution from the desalting procedure described in Example 3 was passed into the column A1, after which 2 l of water were introduced at a feed rate of 8 l/h for displacement of the previously introduced solution.

There were introduced successively into column A2 7.5 l of 4% aqueous sodium hydroxide solution at a feed rate of 4 l/h for the regeneration of the adsorbed components, and 4 l of water at a feed rate of 8 l/h for the displacement of the sodium hydroxide solution.

The eluate from column A2 was introduced directly into column A1. After passage through column A1 the following eluate fractions were collected:

$1^{st}$ fraction, of density less than 1.01 g/ml, being approx. 12 kg of water;

$2^{nd}$ fraction, of density 1.01–1.06 g/ml, being approx. 0.3 kg of a solution E;

$3^{rd}$ fraction, of density 1.06–1.10 g/ml, being approx. 0.3 kg of a solution F; and $4^{th}$ fraction, of density greater than 1.10 g/l, being approx. 3 kg of a solution G.

The solution E contained sodium salts of L-ascorbic acid, phosphoric acid and some L-ascorbyl 2-monophosphate, and can be recycled to the phosphorylation process for producing further ascorbyl monophosphate. The solution F contained only a small amount of the remaining L-ascorbic acid and can be recycled to the next batch for separation.

The solution G contained principally L-ascorbyl 2-monophosphate monosodium salt as the dissolved component. After neutralization with 28% aqueous sodium hydroxide solution to pH 9.5 the solution was analyzed by HPLC. According to the analysis the content of L-ascorbic acid was 18%, of which 1% was non-phosphorylated, 97% was in the form of the monophosphate, 1.5% was in the form of bis-(L-ascorbyl) phosphate and 0.5% was in the form of L-ascorbyl diphosphate. Other polyphosphates were not detected.

After collection of the solution G the column A1 contains the solution D and is ready for the next run.

From the column A2 there were collected two eluate fractions:

$5^{th}$ fraction, of density 1.10–1.05 g/ml, being approx. 2.5 kg of a solution H; and $6^{th}$ fraction, of density 1.05–1.00 g/ml, being approx. 3.5 kg of a solution I.

The solution H contained L-ascorbyl mono- and polyphosphates and pyrophosphoric acid, and was recycled to the phosphorylation process. The solution I consisted largely of dilute sodium hydroxide solution and can be discarded or reused as a basifying solution.

Thereafter, the column A2 is in a state of preparedness for the next run and functions as the column A1.

The invention being thus described, it will be obvious that the same may be varied in many ways. Such variations are not to be regarded as a departure from the spirit and scope of the invention and all such modifications are intended to be included within the scope of the following claims.

What is claimed is:

1. A process for separating L-ascorbyl 2-monophosphate from a desalted mixture obtained from phosphorylation of an L-ascorbic acid salt under basic conditions comprising:
   (a) contacting an aqueous solution of the desalted mixture containing L-ascorbyl 2-monophosphate with a basic anion exchange resin in a separation vessel, wherein the L-ascorbyl 2-monophosphate is adsorbed to the resin;

(b) eluting the L-ascorbyl 2-monophosphate from the resin with an aqueous alkali hydroxide solution; and (c) isolating the L-ascorbyl 2-monophosphate in a corresponding mono-alkali metal salt form from a fraction of the eluate which contains the L-ascorbyl 2-monophosphate in a corresponding mono-alkali metal salt form.

2. A process according to claim 1 wherein the basic anion exchange resin is a weakly basic anion exchange resin comprising amine groups as functional groups.

3. A process according to claim 1 wherein the aqueous alkali hydroxide solution is an aqueous sodium hydroxide solution or aqueous potassium hydroxide solution.

4. A process according to claim 3 wherein the aqueous alkali hydroxide solution is an aqueous sodium hydroxide solution.

5. A process according to claim 1 wherein the concentration of the aqueous alkali hydroxide solution is about 3% to about 6% by weight.

6. A process according to claim 5 wherein the concentration of the aqueous alkali hydroxide solution is about 4% to about 5% by weight.

7. A process according to claim 1 wherein about 1.5 to about 2.0 moles of alkali hydroxide solution per mole of total capacity of the resin are passed through the separation vessel.

8. A process according to claim 1 wherein the volume of the basic anionic exchange resin present is 1 liter resin per 0.5 to 1.5 moles of acid components in the desalted mixture.

9. A process according to claim 1 wherein a rate of flow of the aqueous solutions through the basic anion exchange resin column is from about 0.5 to about 2 bed volumes/hour.

10. A process according to claim 1 wherein acid components of the desalted mixture are dissolved in about 1 to about 5 volumes of water per volume of the resin.

11. A process according to claim 1 further comprising passing water through the resin prior to step (b).

12. A process according to claim 1 further comprising neutralizing the mono-alkali metal salt of L-ascorbyl 2-monophosphate in the collected eluent fraction with aqueous alkali hydroxide solution at a pH of about 9 to about 9.5.

13. A process according to claim 12 wherein the pH is about 6 to about 7.

14. A process according to claim 12 further comprising crystallizing the alkali metal salt of the L-ascorbyl 2-monophosphate.

15. A process according to claim 14 wherein the crystallization is effected by spray drying.

16. A process according to claim 14 wherein the crystallization is effected by treating the mono-alkali metal salt of L-ascorbyl 2-monophosphate with a lower alkanol.

17. A process according to claim 16 wherein the lower alkanol is selected from the group consisting of methanol and ethanol.

18. A process according to claim 12 wherein the collected eluent fraction is concentrated and then crystallized.

19. An eluent consisting essentially of L-ascorbyl 2-monophosphate in a mono-alkali metal salt form isolated according to the process of claim 1.

* * * * *